(12) United States Patent
Raulerson et al.

(10) Patent No.: US 7,806,889 B2
(45) Date of Patent: Oct. 5, 2010

(54) METHOD OF ATTACHING A HUB TO A MULTIPLE CATHETER ASSEMBLY

(75) Inventors: J. Daniel Raulerson, Brewton, AL (US); John Stephens, Perkiomenville, PA (US); Mahase Nardeo, Collegeville, PA (US)

(73) Assignee: Medical Components, Inc., Harleysville, PA (US)

( * ) Notice: Subject to any disclaimer, the term of this patent is extended or adjusted under 35 U.S.C. 154(b) by 285 days.

(21) Appl. No.: 11/592,579

(22) Filed: Oct. 19, 2006

(65) Prior Publication Data

US 2007/0060866 A1   Mar. 15, 2007

Related U.S. Application Data

(62) Division of application No. 10/695,178, filed on Oct. 28, 2003.

(60) Provisional application No. 60/422,726, filed on Oct. 31, 2002, provisional application No. 60/423,002, filed on Nov. 1, 2002.

(51) Int. Cl.
*A61M 25/00* (2006.01)
(52) U.S. Cl. .................................................. 604/523
(58) Field of Classification Search ................. 604/523
See application file for complete search history.

(56) References Cited

U.S. PATENT DOCUMENTS 4,037,599 A   7/1977   Raulerson (Continued)

FOREIGN PATENT DOCUMENTS

EP   0 385 168 A   9/1990

(Continued)

OTHER PUBLICATIONS

Court Hearing in Writing, JP-2000-506899 dated Jul. 15, 2008 (2 pages).

(Continued)

*Primary Examiner*—Nicholas D Lucchesi
*Assistant Examiner*—Jason Flick
(74) *Attorney, Agent, or Firm*—Anton P. Ness; Fox Rothschild LLP

(57) ABSTRACT

A multiple catheter assembly (100) including a first catheter (110) having a first proximal end region (112), a first distal end region (114) terminating in a first distal tip (116), and an outer surface (120) defining at least a first lumen (122) extending longitudinally therethrough between a first distal and a first proximal opening. The assembly (100) also includes a second catheter (130) having a second proximal end region (132), a second distal end region (134) terminating in a second distal tip (136), and a second outer surface (140) defining at least a second lumen (142) extending longitudinally therethrough between a second distal and a second proximal opening. The first (122) and second (142) lumens are independent from each other for facilitating simultaneous flow in opposite directions. The outer surfaces (120,140) of the first and second catheters are releasably joined for allowing the first and second distal tips (116,136) and first and second proximal end regions (112,132) to be at least partially longitudinally split from each other. A method of inserting the catheter assembly (100) is also provided that includes a method of attaching a hub to the catheter assembly.

11 Claims, 10 Drawing Sheets

U.S. PATENT DOCUMENTS

| | | | |
|---|---|---|---|
| 4,405,313 A | | 9/1983 | Sisley et al. |
| 4,682,978 A | | 7/1987 | Martin |
| 4,925,452 A | | 5/1990 | Melinyshyn et al. |
| 4,995,387 A | | 2/1991 | Jinotti |
| 5,037,405 A | | 8/1991 | Crosby |
| 5,053,023 A | | 10/1991 | Martin |
| 5,599,328 A | | 2/1997 | Stevens |
| 5,624,413 A | | 4/1997 | Markel et al. |
| 5,718,692 A | | 2/1998 | Schon et al. |
| 5,776,111 A | * | 7/1998 | Tesio .......................... 604/264 |
| 5,800,414 A | | 9/1998 | Cazal |
| 5,807,311 A | | 9/1998 | Palestrant |
| 5,947,953 A | * | 9/1999 | Ash et al. ................... 604/508 |
| 6,001,079 A | | 12/1999 | Pourchez |
| 6,156,016 A | | 12/2000 | Maginot |
| 6,190,349 B1 | | 2/2001 | Ash et al. |
| 6,497,681 B1 | * | 12/2002 | Brenner ................. 604/164.05 |
| 6,663,600 B2 | * | 12/2003 | Bierman et al. ............. 604/174 |
| 6,695,832 B2 | | 2/2004 | Schon et al. |
| 6,719,749 B1 | | 4/2004 | Schweikert et al. |
| 6,758,854 B1 | | 7/2004 | Butler et al. |
| 6,969,381 B2 | | 11/2005 | Voorhees |
| 2002/0099326 A1 | | 7/2002 | Wilson et al. |
| 2002/0099327 A1 | | 7/2002 | Wilson et al. |
| 2002/0107475 A1 | | 8/2002 | Maginot |
| 2002/0120224 A1 | | 8/2002 | Zia et al. |
| 2005/0096585 A1 | | 5/2005 | Schon et al. |

FOREIGN PATENT DOCUMENTS

| | | |
|---|---|---|
| EP | 0 836 863 A | 4/1998 |
| WO | WO 03/033049 A2 | 4/2003 |

OTHER PUBLICATIONS

International Search Report mailed Apr. 14, 2004.
International Search Authority Supplemental Search Report dated Apr. 7, 2006 (3 pages) from EP Appli. No. 03777942.8.

* cited by examiner

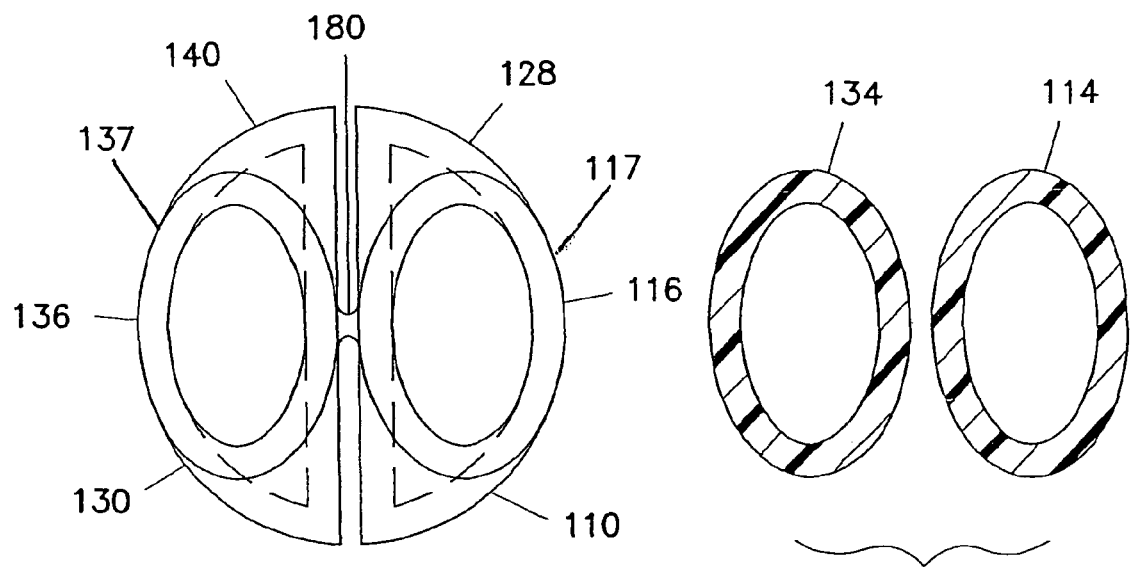
FIG. 4
FIG. 3
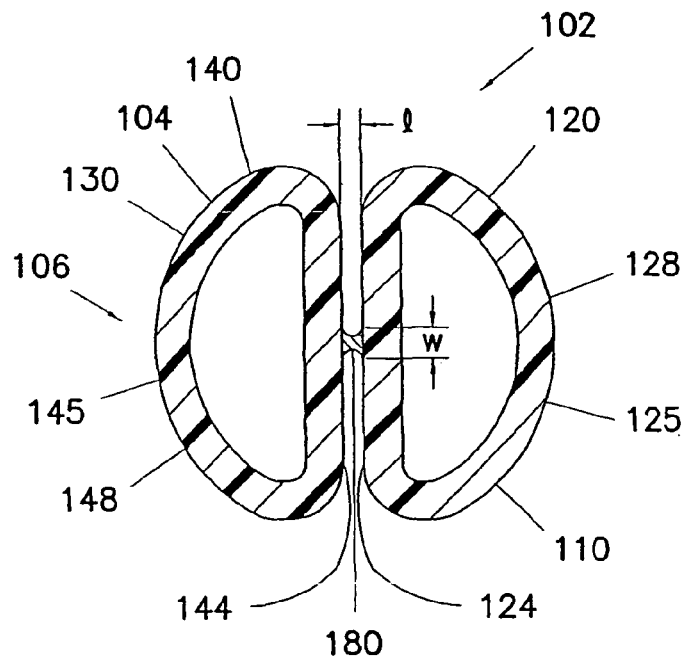
FIG. 2

METHOD OF ATTACHING A HUB TO A MULTIPLE CATHETER ASSEMBLY

CROSS-REFERENCE TO RELATED APPLICATIONS

The present application is a Divisional application of U.S. patent application Ser. No. 10/695,178 filed Oct. 28, 2003, which claims the benefit of U.S. Provisional Patent Application Ser. No. 60/422,726, filed Oct. 31, 2002 and U.S. Provisional Patent Application Ser. No. 60/423,002, filed Nov. 1, 2002.

FIELD OF THE INVENTION

The present invention relates to splittable multiple catheter assemblies, typically used for hemodialysis.

BACKGROUND OF THE INVENTION

Catheters for the introduction or removal of fluids may be located in various venous locations and cavities throughout the body for introduction or removal of these fluids. Such catheterization may be performed by using a single catheter having multiple lumens. A typical example of a multiple lumen catheter is a dual lumen catheter assembly in which one lumen introduces fluid and the other lumen removes fluid. An example of such a dual lumen catheter assembly is the SPLIT CATH® catheter, manufactured and sold by Medical Components, Inc. of Harleysville, Pa.

Generally, to insert any catheter into a blood vessel, the vessel is identified by aspiration with a long hollow needle in accordance with the well known Seldinger technique. When blood enters a syringe attached to the needle, indicating that the vessel has been found, a thin guide wire is then introduced, typically through a syringe needle or other introducer device into the interior of the vessel. The introducer device is then removed, leaving the guide wire within the vessel. The guide wire projects beyond the surface of the skin. At this point, several options are available to a surgeon for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire, for example, for insertion of small diameter dual lumen catheters. If the catheter to be inserted is significantly larger than the guide wire, a dilator device is passed over the guide wire to enlarge the hole. The dilator is removed and the catheter is then passed over the guide wire. After the catheter is inserted, the guide wire is removed.

For chronic catheterization, in which the catheter is intended to remain inside the patient for extended period of time, such as for weeks or even months, it is typically desired to subcutaneously tunnel the catheter using various tunneling techniques. The catheter is typically tunneled into the patient prior to inserting the catheter into the patient's vein. At some point after tunneling, the catheter hub is sutured onto the patient's skin to secure the proximal end of the catheter to the patient.

However, there may be times when it is more advantageous, such as depending on the patient or the implanting surgeon's skill, to perform the tunneling after the catheter is implanted in the patient. For some catheters, though, such as multiple lumen catheters with a hub and with bonded luers on the proximal ends of the catheters, it is impractical to perform the tunneling after the catheter is installed in the patient. It would be beneficial to provide a catheter assembly that provides a surgeon with alternative installation procedures for installing the catheter that better suit either the patient's needs or the surgeon's skills.

Further, for chronically installed catheters, portions of the catheter external to the patient occasionally fail, such as for instance, by leaking and/or by the introduction of foreign particles such as dirt, bacteria, and the like into the catheter, necessitating removal of the entire catheter from the patient. Such failures include worn or broken clamps or broken luers. In order to correct these problems, it is presently necessary to remove the entire catheter from the patient, causing additional trauma to the patient and risking additional medical problems to the patient. It would be beneficial to provide a catheter in which the proximal portion of the catheter may be removed and replaced without disturbing the distal portion of the catheter inside the patient.

Also, while catheter assemblies typically are manufactured in standard sizes, such as 12 French, 14 French, etc., patients come in many various shapes and sizes. Where a particular size catheter may be an optimum size for one patient, the surgeon may desire or require a different length of a subcutaneous tunnel for a different patient. However, the location of the catheter hub may dictate the length and/or location of the subcutaneous tunnel. It would be beneficial to provide a catheter assembly that has an adjustable location for the hub along the catheter assembly to provide the surgeon options for securing the catheter assembly to the patient.

BRIEF SUMMARY OF THE INVENTION

Briefly, the present invention provides a multiple catheter assembly. The assembly includes a first catheter having a first proximal end region, a first distal end region terminating in a first distal tip, and an outer surface defining at least a first lumen extending longitudinally therethrough between a first distal and a first proximal opening. The assembly also includes a second catheter having a second proximal end region, a second distal end region terminating in a second distal tip, and a second outer surface defining at least a second lumen extending longitudinally therethrough between a second distal and a second proximal opening. The first lumen and the second lumen are independent from each other for facilitating simultaneous flow in opposite directions. The outer surfaces of the first and second catheters are releasably joined for allowing the first and second distal tips and first and second proximal end regions to be at least partially longitudinally split from each other.

Additionally, the present invention provides a method for inserting a multiple catheter assembly into an area of a body to be catheterized. The method comprises making an incision near the area to be catheterized; providing a multiple catheter assembly comprising a first catheter having a first proximal end region, a first distal end region terminating in a first distal tip, and a first outer surface defining at least a first longitudinally extending lumen; and a second catheter having a second proximal end, a distal end region terminating in a distal tip, and a second outer surface defining at least a second longitudinally extending lumen; wherein the outer surfaces of each of the first and second catheters are releasably joined and each of the first and second lumens are independent from each other for facilitating simultaneous flow in opposite directions, wherein the outer surfaces of each of the first and second catheters are releasably joined for allowing each of the first and second distal tips and first and second proximal ends to be at least partially longitudinally split from each other; at least partially separating the first and second distal end regions of the first and second catheters from each other; and inserting the first and second distal end regions of the first and second catheters in juxtaposed relation to each other through the incision and into the area to be catheterized.

Further, the present invention provides a method of releasably attaching a hub to a catheter, wherein the hub comprises two hingedly connected opposing portions, each portion having an inner face and an outer face, at least one channel to accommodate at least one lumen of a catheter disposed on the inner face of at least one of the two hingedly connected opposing portions, and a means for remaining releasably locked in the closed position. The method comprises placing the at least one lumen of a catheter in the at least one channel of at least one of the two hingedly connected opposing portions; folding the other of the two hingedly connected opposing portions over the at least one lumen thereby mating the inner face of one of the two hingedly connected opposing portions with the inner face of the other of the two hingedly connected opposing portions and fitting the two hingedly connecting portions around the at least one lumen; and releasably locking the hub in the closed position.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 2 is an enlarged sectional view of the catheter lumens of the catheter assembly taken along lines 2-2 of FIG. 1.

FIG. 3 is an enlarged sectional view of the distal end of the catheter lumens of the catheter assembly taken along lines 3-3 of FIG. 1.

FIG. 4 is an enlarged end view of the distal end of the catheter lumens of the catheter assembly taken along lines 1-4 of FIG. 1.

DETAILED DESCRIPTION OF THE INVENTION

Figure 1:
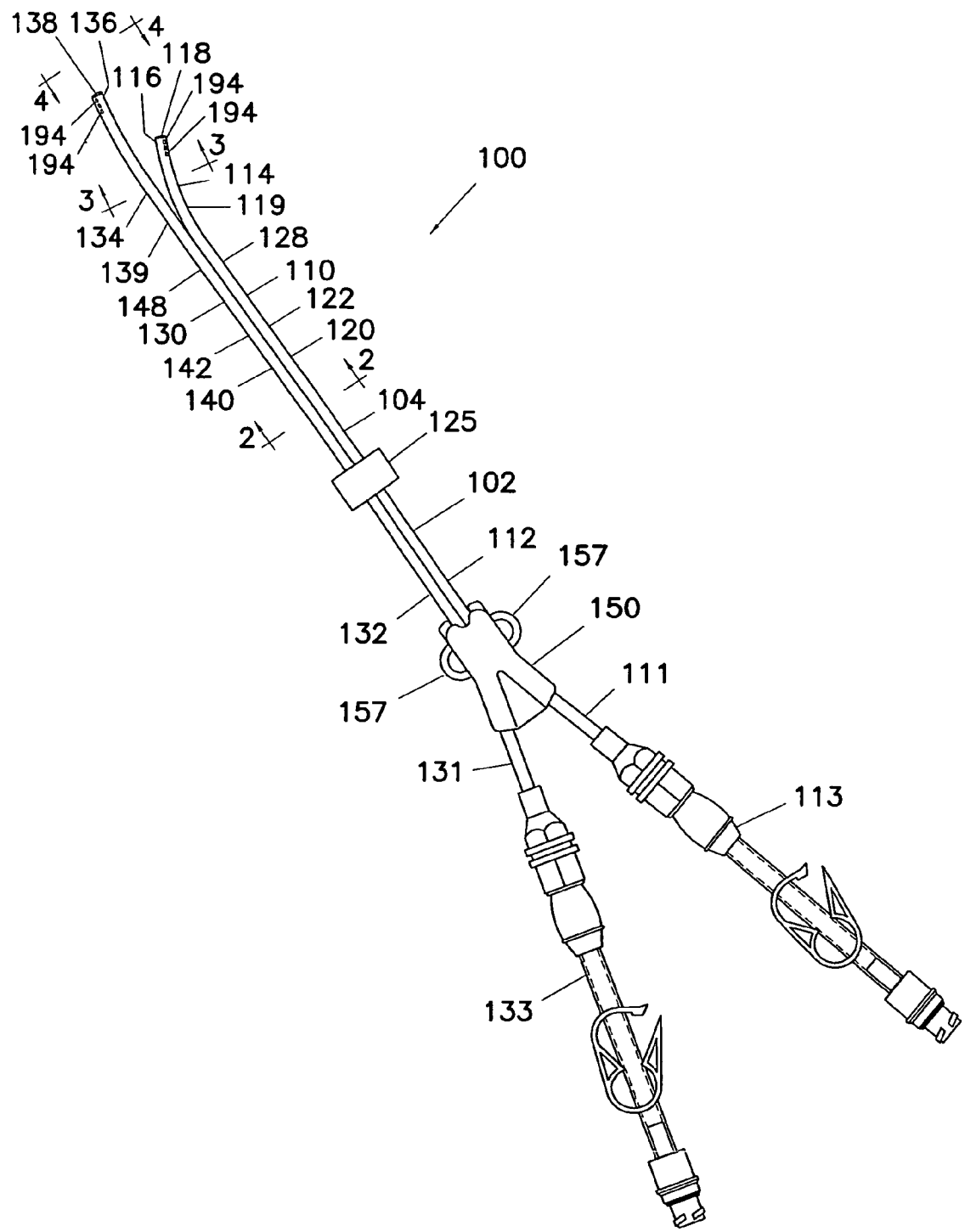
FIG. 1 is a top plan view of a catheter assembly according to a preferred embodiment of the present invention.

In the drawings, like numerals indicate like elements throughout. Certain terminology is used herein for convenience only and is not to be taken as a limitation on the present invention. The terms "distal" and "proximal" refer, respectively, to the directions "away from" and "closer to" the surgeon inserting the catheter into a patient. The terminology includes the words above specifically mentioned, derivatives thereof, and words of similar import.

The following describes preferred embodiments of the invention. However, it should be understood, based on this disclosure, that the invention is not limited by the preferred embodiments described herein. Referring now to the drawings in detail, there is shown in FIG. 1, an embodiment of a multiple catheter assembly generally indicated as 100. The multiple catheter assembly 100 shown in FIG. 1 is a double catheter assembly, although assemblies having two or more catheters are within the scope of this invention.

The invention as shown in this disclosure is preferably useful for the removal of blood for purification from a blood vessel, such as the internal jugular vein, and introduction of purified blood into the same vessel. However, it will be known to those skilled in the art that the multiple catheter assembly 100 may be used to introduce or remove various fluids in various areas to be catheterized.

The multiple catheter assembly 100 includes a cannulating portion 102 defined by an outer surface 104. The multiple catheter assembly 100 further includes a first catheter 110 at least partially releasably joined to a second catheter 130. The first catheter 110 includes a first proximal end region 112, and a first distal end region 114 having a first distal tip 116. The first distal tip 116 has a first distal opening 118. The first catheter 110 also has a first outer surface 120 defining a first lumen 122. The first lumen 122 fluidly communicates with the first distal opening 118. The second catheter 130 includes a second proximal end region 132, and a second distal end region 134 having a second distal tip 136. The second distal tip 136 has a second distal opening 138. The second catheter 130 also has a second outer surface 140 defining a second lumen 142. The second lumen 142 fluidly communicates with the second distal opening 138. Preferably, the first distal tip 116 ends approximately 2.5 cm proximate of the second distal tip 136. The first catheter 110 is preferably an arterial lumen used to draw fluid, such as blood, from the patient, while the second catheter 130 is preferably a venous lumen used to return the fluid to the patient after processing, such as by hemodialysis. The approximate 2.5 cm distance difference between the first distal tip 116 and the second distal tip 136 serves to reduce recirculation of the fluid that has already been processed.

As shown in FIG. 2, in the cannulating portion 102 of the multiple catheter assembly 100, each of the first catheter 110 and the second catheter 130 comprise semicircular cross-sections 128, 148, respectively. Accordingly, the first outer surface 120 is defined by a first generally flat portion 124 and a first rounded wall portion 125. Likewise, the second outer surface 140 is defined by a second generally flat portion 144 and a second rounded wall portion 145. Preferably, the first generally flat portion 124 and the second generally flat portion 144 are juxtaposed from each other and are very close to each other, but do not necessarily touch each other. It is also preferable that the first outer surface 120 and the second outer surface 140 are virtually identical to each other so that when the first generally flat portion 124 is very close to the second generally flat portion 144, the outer surface 104 of the cannulating portion 102 has a generally circular cross section 106. It should be understood, based on this disclosure, that the first catheter 110 and the second catheter 130 may be further subdivided and/or additional catheter tubes of the same or varied cross sectional configuration may be provided within the scope of the invention.

The multiple catheter assembly 100 includes a splittable bond 180, which extends longitudinally between and joins the first generally flat portion 124 and the second generally flat portion 144. The splittable bond 180 may be an adhesive used to releasably connect the first generally flat portion 124 and the second generally flat portion 144.

While the generally semi-circular cross section 128, 148 of the first catheter 110 and the second catheter 130 as shown in FIG. 2 corresponding to the cannulating portion 102 of the multiple catheter assembly 100 is the preferred configuration for fluid flow in each of the first lumen 122 and second lumen 142, other configurations may be used without departing from the spirit of the present invention, such as, for example, oval, circular, elliptical, square, triangular, and kidney-bean shaped. A multiple catheter assembly having such luminal configurations may have an accordingly varied cross section. The first lumen 122 and second lumen 142 may be of equal cross sectional or of different cross sectional areas.

While two lumens 122, 142 of equally sized cross sections are shown in FIGS. 2-4, additional catheters having lumens of the same or different cross sectional areas may also be included in the multiple catheter assembly 100. For example, a multiple catheter assembly 100 used for hemodialysis may comprise two catheters of equal cross sectional area for the removal and return of blood and a third catheter with a smaller cross sectional area to be used for the infusion of medication into the patient. In such an embodiment, it is preferable to have the catheters connected by more than one splittable bond. The catheter assembly with such a configuration may also not be circular in cross section in a configuration having unequal cross sectional areas.

It is also possible to subdivide the various catheter lumens 110, 130 within the assembly 100 by providing at least one longitudinally extending septum within a lumen. In this manner, by having a longitudinally extending septum, a dual catheter assembly can provide three or more individual lumens by splitting the individual catheter(s). These and all of the alternative tube configurations are intended to be merely exemplary and illustrative, and by no means is this an inclusive list. It will be understood that the present invention is not limited to the configurations shown or mentioned in this specification or shown in the drawings.

Referring back to FIG. 1, the distal tip of the first catheter 110 includes the first distal opening 118 extending therethrough. Likewise the distal tip 136 of the second catheter 130 includes the second distal opening 138 extending therethrough. Preferably, the distal tips 116, 136 are blunt, in that they are configured to lie generally in a plane which is perpendicular to the longitudinal length of the cannulating portion 102. The distal tips 116, 136 may have a semicircular cross section or a slightly circular cross section. However, in the present embodiment, referring to FIGS. 3 and 4, the distal tips 116, 136 comprise a first distal generally oval cross section 117 and a second distal generally oval cross section 137. However, those skilled in the art will recognize that the distal tips 116, 136 may include cross sections of other shapes, such as round, or other suitable shapes. Referring to FIG. 1, it is preferred that the distal tips 116, 136 have a distal transition portion 119, 139, respectively, wherein the cross section transitions from semi-circular, proximally of each distal transition portion 119, 139, to oval, distally of each distal transition portion 119, 139. A plurality of side apertures 194 are located throughout the first distal end region 114 and the second distal end region 134. Specifically, in the preferred embodiment, the plurality of side apertures 194 are located on the first and second generally oval cross sections 117, 137, respectively, although those skilled in the art will recognize that the side apertures may also or alternatively be located on the first and second generally semi-circular cross-sections 128, 148 just proximal of each of the distal tips 116, 136. The side apertures 194 on the first semi-circular cross-section are in fluid communication with the first lumen 122 and the side apertures 194 on the second semi-circular cross-section are in fluid communication with the second lumen 142.

Figure 5:
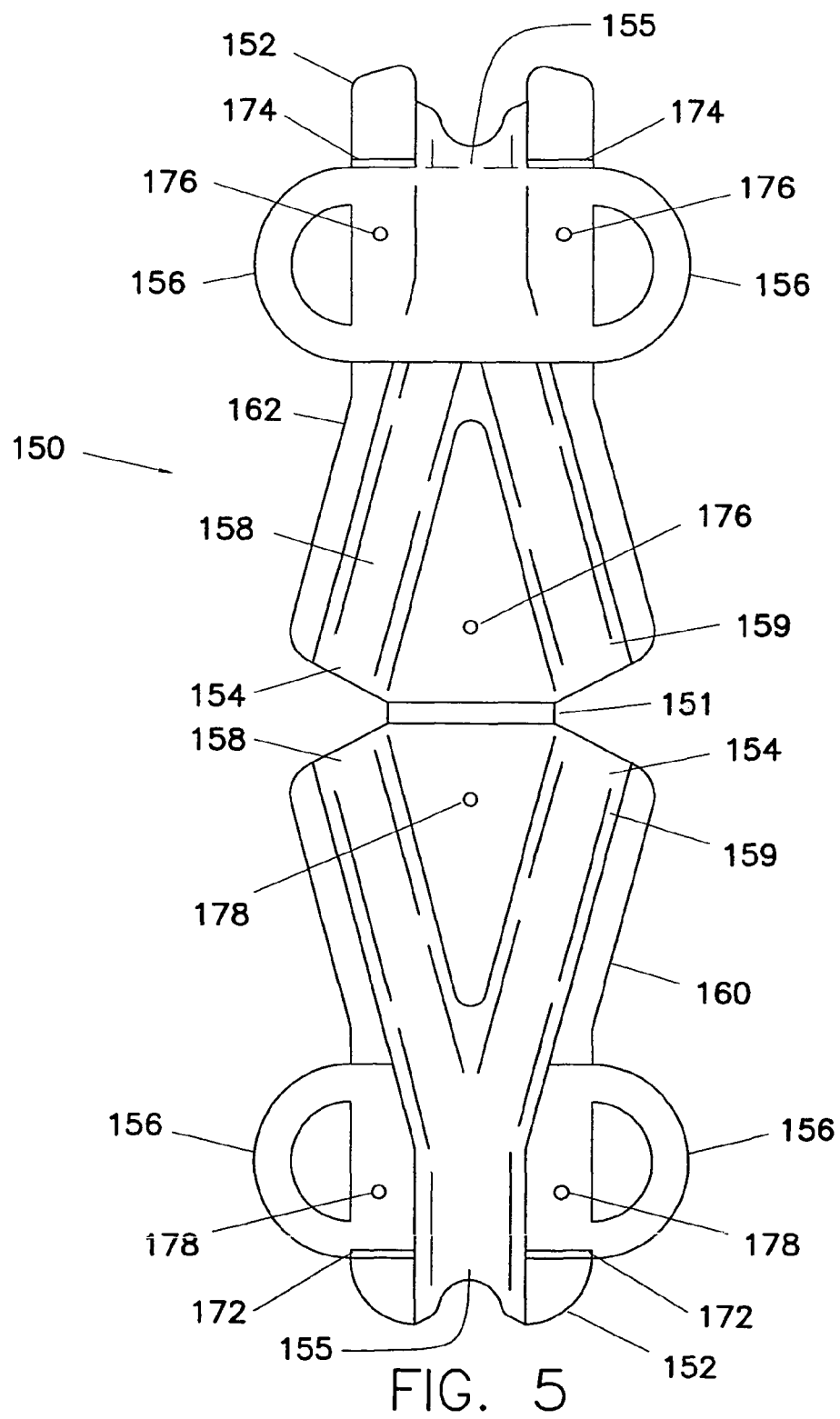
FIG. 5 is an enlarged top plan view of a catheter hub according to an embodiment of the present invention in an open position.
Figure 6:
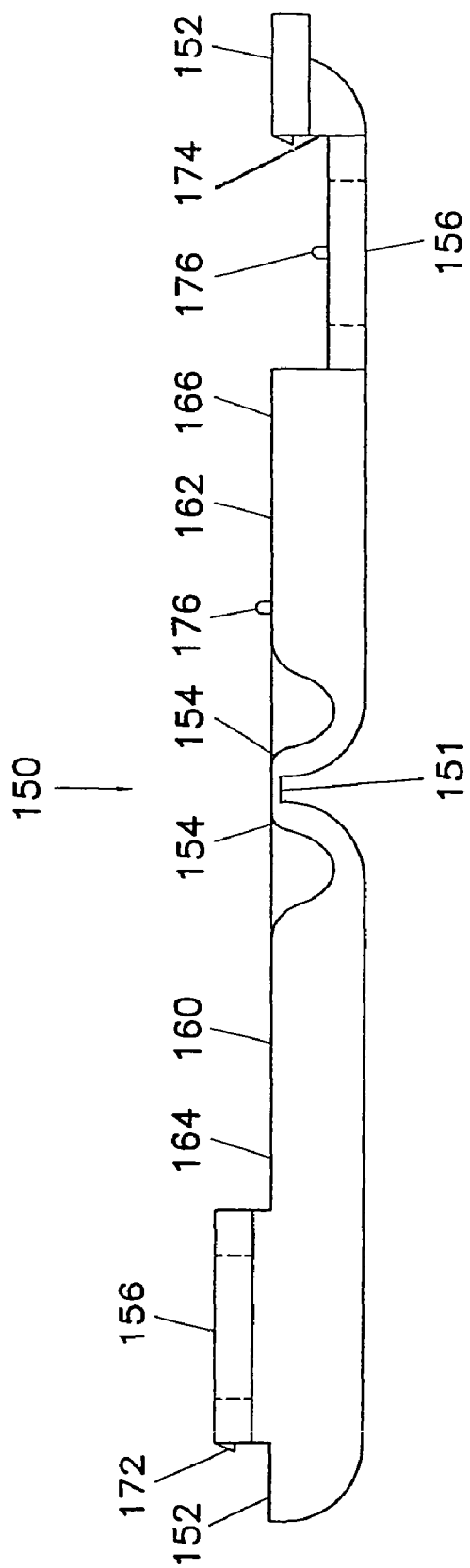
FIG. 6 is a side view of the hub of FIG. 5.
Figure 12:
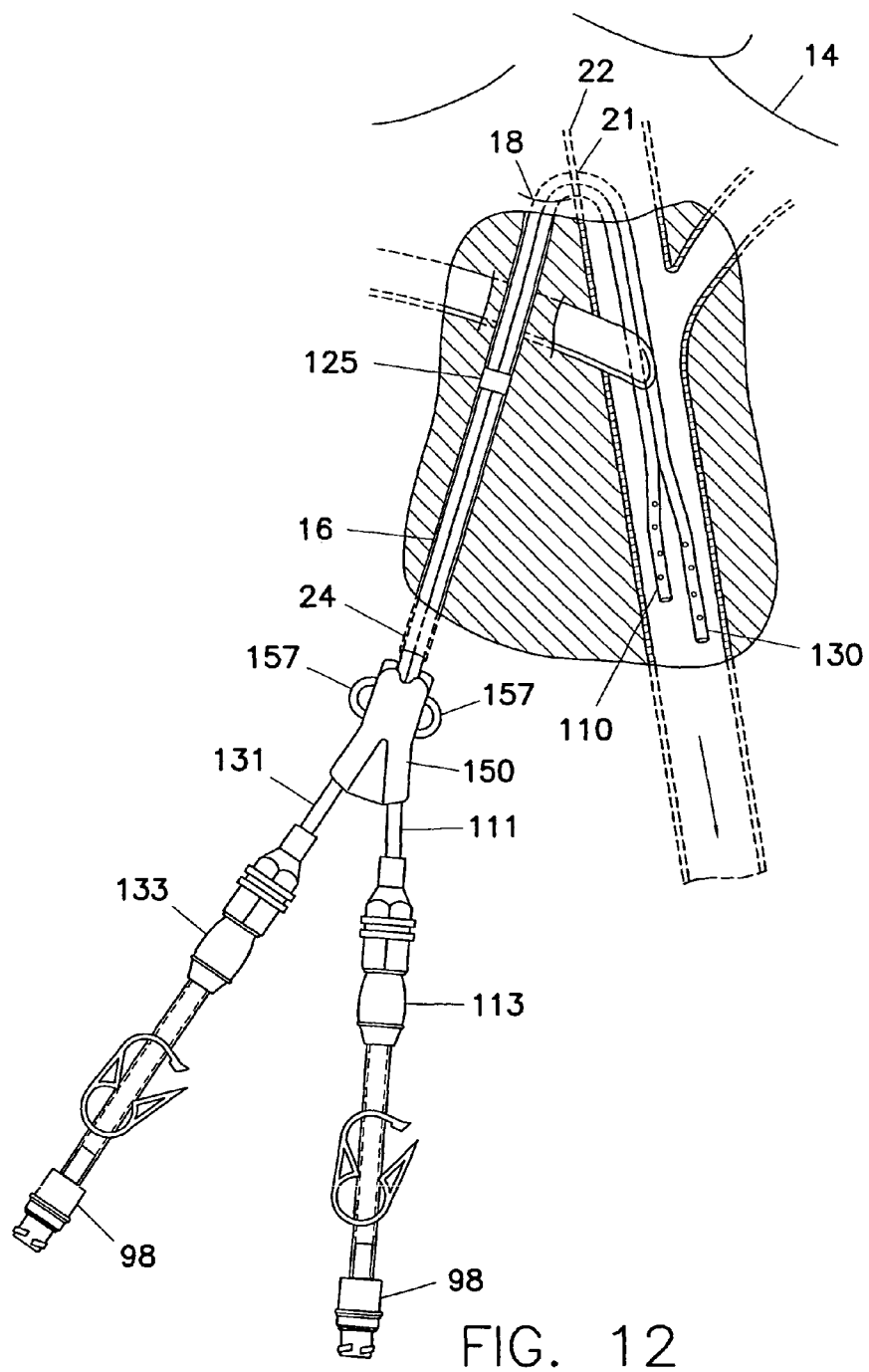
FIG. 12 is a partially broken away diagrammatic view of the multiple catheter assembly of FIG. 10, with a hub and catheter extension connected to the proximal portion of the catheter assembly, in accordance with one embodiment of inserting a multiple catheter assembly according to the present invention.

Still referring to FIG. 1, a longitudinally translatable hub 150 is releasably connected to the proximal regions 112, 132 of the first and second catheters 110, 130, respectively. A preferred hub 150 is disclosed in U.S. Pat. No. 7,261,708, which is incorporated by reference herein in its entirety as though fully set forth, although those skilled in the art will recognize that other hub designs may be used, or that the hub 150 may be omitted in its entirety. The hub 150, as shown in FIGS. 1, 5, and 6, is operable between an open position and a closed position and has a distal end 152 and a proximal end 154. The hub 150 is designed to allow both of the catheters 110, 130 in the multiple catheter assembly 100 to enter the distal end 152 of the hub 150 together. A distal channel 155 runs longitudinally through the hub 150 to house the catheters 110, 130. At a predetermined point along the hub 150, the distal channel 155 branches out or diverges, from the single distal channel 155, near the distal end 152 of the hub 150, to a first proximal channel 158 and a second proximal channel 159 near the proximal end 154 of the hub 150. Each of the first proximal and second proximal channels 158, 159 houses one or more individual catheters 110, 130 but less than the number of catheters housed by the distal channel 155. In the present embodiment, as shown in FIGS. 1, 5, and 6, the distal end 152 of the hub 150 is designed to juxtapose the first catheter 110 and second catheter 130 against each other and the proximal end 154 of the hub 150 is designed to separate the first catheter 110 from the second catheter 130. The catheters 110 and 130 extend completely through the hub and diverge between the distal and proximal hub ends, with proximal catheter end sections 111, 131 projecting beyond the proximal hub end 154, as is seen in FIG. 12. The hub 150 may also be slid longitudinally along the multiple catheter assembly 100. The distal channel 155 and the first and second proximal channels 158, 159 of the hub are sized so that the hub 150 may frictionally maintain its place on the multiple catheter assembly 100.

Referring to FIGS. 5 and 6, the hub 150 comprises a top hub portion 160 and a bottom hub portion 162. The top and bottom hub portions 160, 162 are hingedly connected by a hinge 151 at the proximal end 154 of the hub 150. The hinge 151 is located between the first proximal channel 158 and the second proximal channel 159. The top hub portion 160 is adapted to mate to the bottom hub portion 162, when the hub 150 is in a closed position. The distal channel 155 and the first and second proximal channels 158, 159 are partially disposed on the inner face 164 of the top hub portion 160 as well as on the inner face 166 of the bottom hub portion 162 so that when the hub 150 is in the closed position, the inner face 164 of the top hub portion 160 mates with the inner face 166 of the bottom hub portion 162 and the distal and first and second proximal channel 155, 158, 159 run through the hub 150. The hub 150 releasably locks in the closed position. The top hub portion 160 includes tabs 172, which snap into recesses 174 in the bottom hub portion 162. The tabs 172 and recesses 174, as well as raised bumps 176 on the bottom hub portion 162, which mate to small indentations 178 on the top hub portion 160, ensure the rigidity of the hub 150 when in the closed position. Although a snapping tab and recess mechanism is disclosed here, this invention anticipates a wide array of means for releasably locking the top hub portion 160 and the bottom hub portion 162 in the closed position.

The hub 150 is releasably attachable to a patient. The hub 150 includes a plurality of suture wings 156 protruding therefrom, which may be releasably attached to a patient. The suture wings 156 protrude from the hub 150 on either side of the distal channel 155 as shown in FIG. 5. Four suture wings 156 are positioned on the top hub portion 160 and the bottom hub portion 162 such that when the hub 150 is in the closed position, the four suture wings 156 align to form two suture wing assemblies 157, shown in FIG. 1. In the present embodiment, the suture wing assemblies 157 are adjacent to the tabs 172 and recesses 174, but they may be located anywhere on the hub 150. With the suture wing assemblies 157 located in a position away from the hinge 151, they can be used to assist in securing the hub 150 in the closed position. Furthermore, this invention anticipates other means for releasably attaching a hub 150 to a patient. Further, while two suture wing assemblies 157 are shown in FIG. 1, those skilled in the art will recognize that more or less than two suture wing assemblies 157 may be used.

Figures 7, 8:
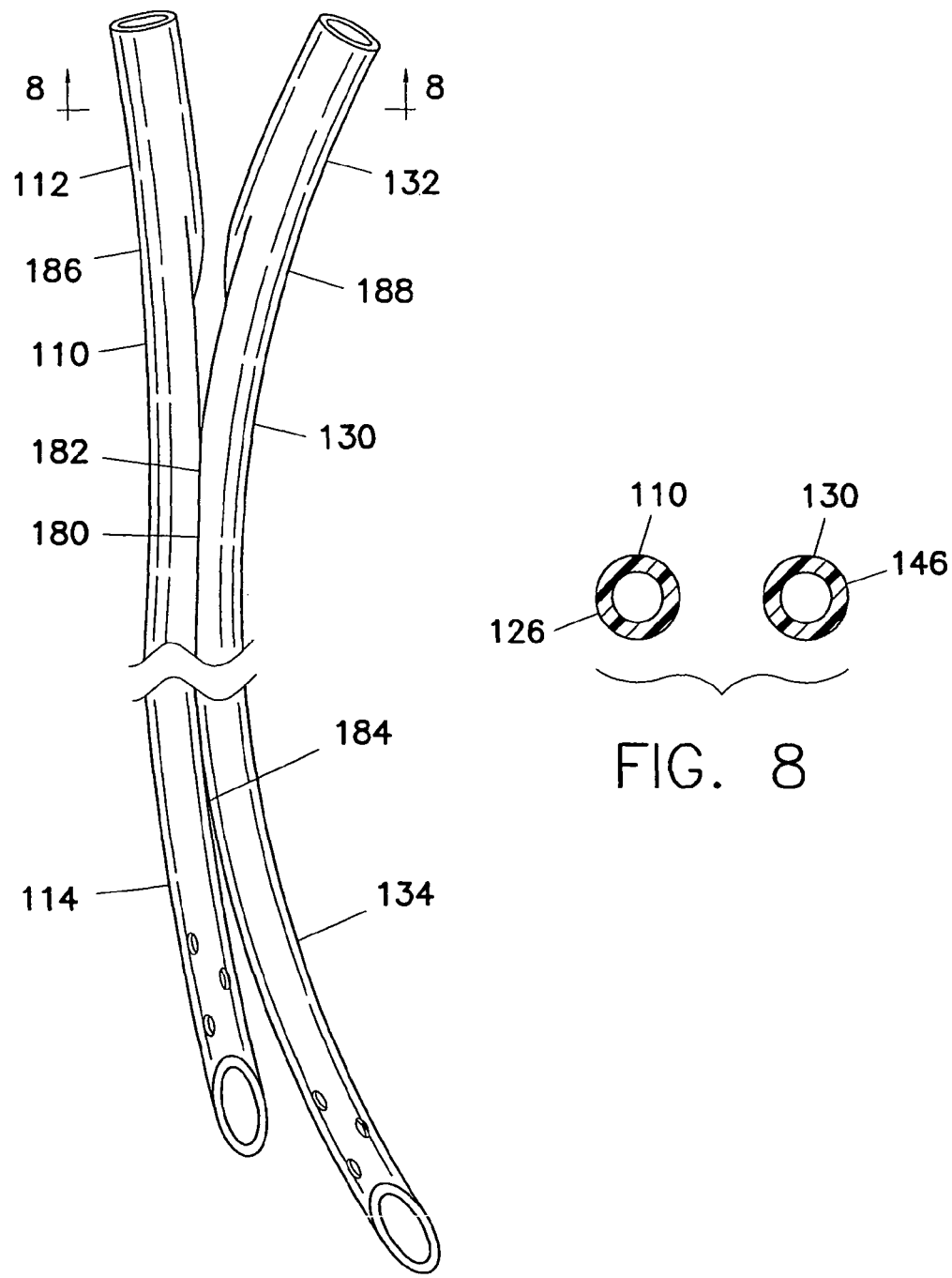
FIG. 7 is a top plan view of the catheters only from the catheter assembly of FIG. 1.
FIG. 8 is a sectional view of the catheters taken along lines 8-8 of FIG. 7.

Referring now to FIG. 7, which shows the catheters 110, 130 only, a splittable bond 180 releasably connects the first catheter 110 to the second catheter 130 in the cannulating portion 102 thereof. The splittable bond 180 includes a distal end 184 and a proximal end 182, either or both of which may be split to allow the proximal end regions 112, 132 and the distal end regions 114, 134 of the first catheter 110 and second catheter 130, respectively, to be manipulated independently of each other.

The splittable bond 180 performs multiple functions. First, the splittable bond 180 joins the first catheter 110 and the second catheter 130 so that the first catheter 110 and second catheter 130 may be easily manipulated together, particularly along the section of the first catheter and second catheter 130 where the splittable bond 180 is unbroken. If the splittable bond 180 is intact, the first catheter 110 and the second catheter 130 may be manipulated as a single catheter. Second, the splittable bond 180 allows the first catheter 110 and the second catheter 130 to be at least partially longitudinally split apart from each other without damaging the outer surface of the first catheter 110 or the second catheter 130. Splitting the distal end 184 of the splittable bond 180 allows independent movement of the first distal end region 114 and the second distal end region 134 in the vessel or other area to be catheterized. Conversely, splitting the proximal end 182 of the splittable bond 180 allows independent movement of the first proximal end region 112 and the second proximal end region 132. Such independent movement allows for longitudinal translation of the hub 150 (not shown in FIG. 7) along a length of the catheter assembly 100. The splittable bond 180 is constructed to split easily when the first catheter 110 and the second catheter 130 are forcibly pulled apart from each other. It is preferred, as shown in FIG. 2, that the splittable bond 180 has a cross sectional width "w" at its thinnest point which is a very small fraction of the outer diameter of the multiple catheter assembly 100 to facilitate easy tearing.

The splittable bond 180 is also constructed of a material, such as an adhesive, that will tear before the forces exerted in the outer surfaces of either the first catheter 110 or second catheter 130 reach a level that will cause damage thereto. However, the splittable bond 180 should be sufficiently strong to resist tearing during normal handling of the multiple catheter assembly 100. The splittable bond 180 has a cross sectional length "l" which is also a small fraction of the outer diameter of the multiple catheter assembly 100. The cross sectional length "l" of the splittable bond 180 also defines the distance between the first generally flat surface 124 and the second generally flat surface 144. The cross sectional length "l" of the splittable bond 180 is preferably small enough to maintain an overall generally circular cross section 104, and to facilitate handling of the unseparated cannulating portion 102 of the multiple catheter assembly 100.

Referring back to FIG. 7, the proximal portion 112, 132 of each of the first and second catheters 110, 130 includes a first transition portion 186 and a second transition portion 188, respectively. These transition portions 186, 188 comprise a change in the cross sectional profile of the first and second catheters 110, 130. Specifically, distally of the first transition portion 186, the first catheter 110 has a generally semi-circular cross section 128, as shown in FIG. 2, whereas proximally of the first transition portion 186, the first catheter 110 has a generally circular cross section 126, as shown in FIG. 8. Similarly, distally of the second transition portion 188, the second catheter 130 has a generally semi-circular cross section 148, whereas proximally of the second transition portion 188, the second catheter 130 has a generally circular cross section 146. The first transition portion 186 and second transition portion 188 are located in the very near proximity of the proximal end 182 of the splittable bond 180. The first generally flat surface 124 and second generally flat surface 144, that are joined by the splittable bond 180, each end at the first transition portion 186 and second transition portion 188.

Referring back to FIG. 1, a first extension tube assembly 113 and a second extension tube assembly 133 are attached to the first proximal end 111 and the second proximal end 131, respectively. For illustrative purposes, the first extension tube assembly 113 is shown in an exploded view in FIG. 9. While an exploded view of the second extension tube assembly 133 is not shown, those skilled in the art will recognize that the second extension tube assembly 133 includes the same components as the first extension tube assembly 113.

Each extension tube assembly 113, 133 includes an extension tube 196, a luer connector 198 connected to a proximal end of each extension tube 196, and a male threaded connector portion 200 connected to a distal end of each extension tube 196. A clamp 202, such as a Roberts clamp, or some other suitable clamp known to those skilled in the art, is disposed over each extension tube 196 between each luer connector 198 and each male threaded connector portion 200. Each clamp 202 is operable between an open condition that allows fluid flow through each respective extension tube 196 and a closed condition that precludes fluid flow through each respective extension tube 196.

An extension tube connector 204 extends from each male threaded connector portion 200. Each extension tube connector 204 is sized to be inserted into the proximal end openings 111, 131 of each of the first catheter 110 and the second catheter 130, respectively. A barb 205 may extend from the tube connector 204 to retain the proximal end 112, 132 of each of the first and second lumens 110, 130, although those skilled in the art will recognize that more than one barb 205 may be used, or that the barb 205 may be omitted in its entirety. A compression fitting 206 is disposed over the exterior of each catheter 110, 130 and over each extension tube connector 204. A female threaded connector portion 208 is disposed over each compression fitting 206 and is threadedly connected to each respective male threaded connector portion 200, securing each extension tube assembly 113, 133 to each respective catheter lumen 110, 130 and providing for fluid communication between the extension tube assemblies 113, 133 and each respective catheter lumen 110, 130.

Referring back to FIG. 1, a fabric cuff 125 is disposed on a portion of the exterior of the catheters 110, 130, preferably approximately halfway between the proximal end regions 112, 132 and the distal end regions 114, 134 of the catheters 110, 130. The portion of the catheter 110, 130 located distal of the cuff 125 are inserted into the patient through an incision during catheterization, and the portion of the catheters 110, 130, as well as the remaining portions of the catheter assembly 100, remain exterior of the incision. The cuff 125 provides a surface for the patient's skin to graft to the catheter assembly 100. Preferably, the cuff 125 is constructed from DACRON® polyester or some other, suitable, biocompatible fabric.

Preferably, the first and second catheters 110, 130 are constructed from a biocompatible polyurethane, such as TECOTHANE® or CARBOTHANE® polyurethane, although those skilled in the art will recognize that other materials, such as biocompatible plastics such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art may be used. It should be understood that these possible biocompatible materials are included above for exemplary purposes and should not be construed as limiting. If a biocompatible polymeric material is used to form the first and second catheters 110, 130, it is most preferred that the polymeric material includes a polyurethane or a polyolefin polymeric material having a preferably soft durometer.

Other suitable, preferred, biocompatible elastomers for use in forming the catheters 110, 130 include biocompatible elastomers such as medical grade silicone rubbers, polyvinyl chloride elastomers, polyolefin homopolymeric and copolymeric elastomers, urethane-based elastomers, and natural rubber or other synthetic rubbers. Preferably, the catheters 110, 130 are made of the elastomeric material such that they are flexible, durable, soft, and easily conformable to the shape of the area to be catheterized and/or a subcutaneous area and minimize risk of harm to vessel walls. If the catheters 110, 130 are used for hemodialysis applications, they are preferably formed of a soft silicone elastomer which has a hardness of at least about 80-A on a Shore durometer scale. Such an elastomer is available from Dow Corning, and can include 20% barium sulfate in the elastomer to provide radiopacity. While it is preferred to have a higher Shore durometer hardness if a biocompatible elastomer is used, particularly for hemodialysis, it is also possible to make a device from an elastomer having a lower Shore durometer hardness without departing from the spirit of the invention. It will be understood, based on this disclosure, that the catheters 110, 130 may also be radiopaque depending on their intended use.

In one preferred embodiment of the present invention, the cannulating portion 102 of the assembly 100 is fabricated by a single extrusion process, injection molding process, or blow molding process. One fabrication process is extrusion. In such a process, the splittable bond 180 may be formed using the same material as the catheters 110, 130. In an alternative embodiment, each catheter 110, 130 and the bond 180 are individually formed, and then joined by suitable manufacturing techniques to become a unitary product. In this alternative process, the bond 180 may be formed of the same, or different material than the catheters 110, 130, such as an adhesive.

Figure 10:
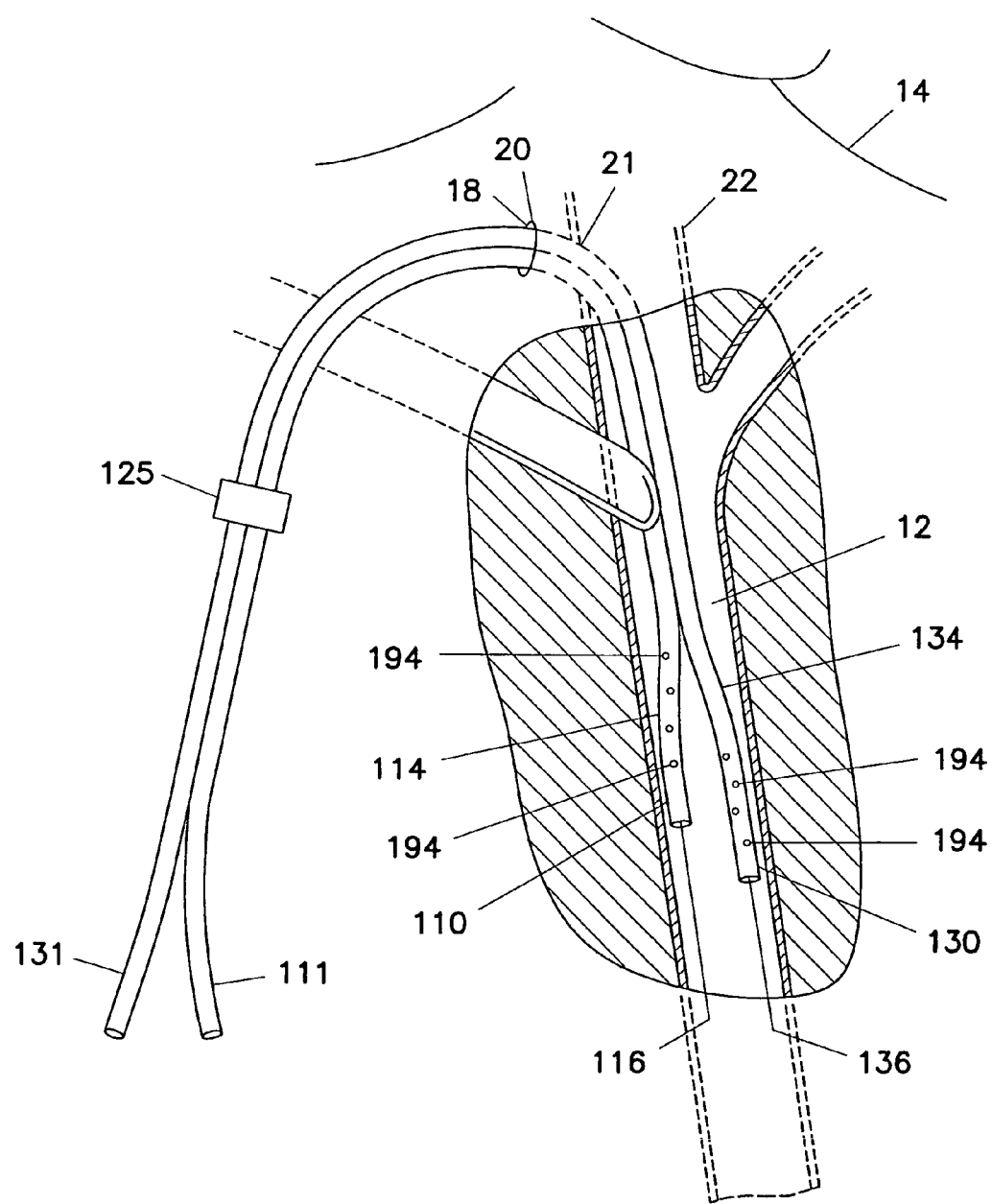
FIG. 10 is a partially broken away diagrammatic view of a multiple catheter assembly which has been partially split and inserted into an area to be catheterized, in accordance with one embodiment of inserting a multiple catheter assembly according to the present invention.
Figure 11:
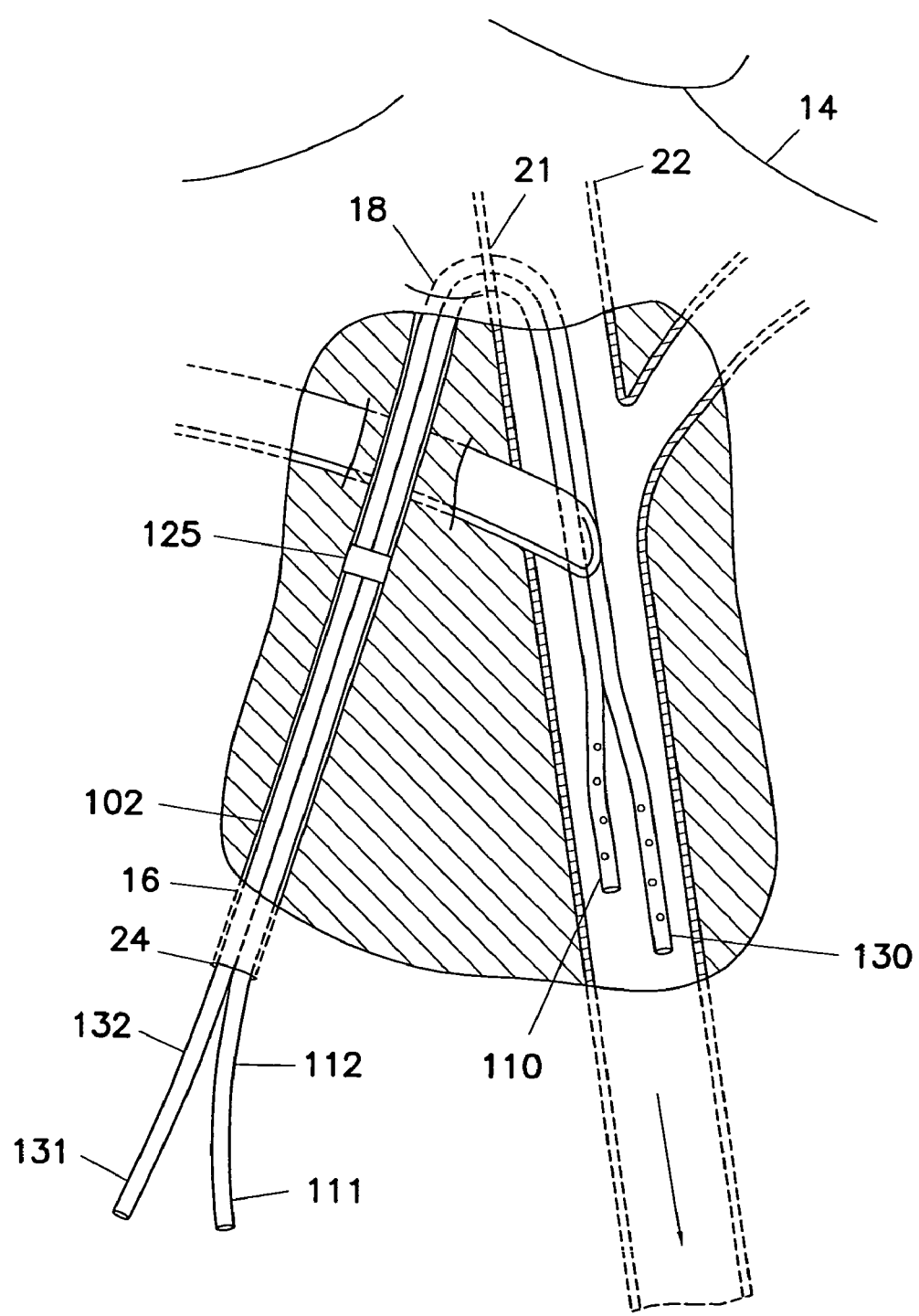
FIG. 11 is a partially broken away diagrammatic view of the multiple catheter assembly of FIG. 10, with a proximal portion of the catheter assembly having been subcutaneously tunneled, in accordance with one embodiment of inserting a multiple catheter assembly according to the present invention.

A preferred method of insertion of the catheter assembly 100 is shown graphically in FIGS. 10 through 12. The catheter assembly 100 is devoid of the hub 150 and the extension tube assemblies 113, 133, so that the catheter assembly 100 appears as shown in FIG. 7. Referring now to FIG. 10, an incision 18 is initially made near an insertion site 20 which is to be aspirated with a syringe or other introducer apparatus near or proximate the area to be catheterized 21 on the patient 14. If the catheter assembly 100 is used for hemodialysis and the area to be catheterized 21 is the internal jugular vein 22, the incision 18 is made in the clavicular triangle region, as shown for example, in FIG. 10. The exact location of the incision 18 may be varied by the surgeon. In accordance with the Seldinger technique, a narrow needle is inserted through the incision 18 and into the vein 21, and the vein 22 is aspirated. A guide wire (not shown) is then passed through the needle, or other introducer, and the needle is removed. A dilator (not shown) and a tearable sheath are introduced over the guide wire and partially into the vein 22. Once the sheath is in place, the dilator and the guide wire are removed, leaving the sheath in place. The insertion site 18 is now ready to accept the catheter assembly 100.

Prior to insertion, the catheter assembly 100 is split along the splittable bond 180 from the distal tip 116 of the first catheter 110 by a longitudinal distance which is at least long enough to allow free flow through all side apertures 194. Preferably, the bond 180 is split along a length of the catheters 110, 130 as desired by the surgeon, up to the ingrowth cuff 125. Preferably, the catheters 110, 130 are already at least partially split along a portion of the distal end regions 114, 134 of the catheters 110, 130 as shown in FIG. 1 prior to insertion, which facilitates splitting of the splittable bond 180. While the user does not have to split the entire length of the bond 180, it is preferred that the bond 180 be fully split for allowing independent movement of the distal end regions 114, 134 of the catheters 110, 130 within the vessel.

After splitting, the distal end regions 114, 134 of the first and second catheters 110, 130 are inserted into, and through, the sheath in juxtaposed relationship. The distal end regions 114, 134 are inserted until they are properly positioned within the area 12, as shown in FIG. 10. The sheath is then removed in the conventional manner, leaving the distal end regions 114, 134 of the first and second catheters 110, 130 in the area 12. As shown in FIG. 10, at least a portion of the distal end regions 114, 134 of each of the catheters 110, 130 may freely move within the area 12.

Referring to FIG. 11, the proximal portions of the catheters 110, 130 may be located within a subcutaneous tunnel 24 in the subcutaneous area 16 of the body 14, using various tunnelling techniques. In one preferred technique, the proximal end regions 112, 132 of the catheters 110, 130 are pulled through the tunnel 24 from the end of the tunnel 24 proximate to the incision 18, while forming the tunnel 24 using a trocar or other tunnelling tool, leaving the proximal end regions 112, 132 at least partially within the tunnel 24, with the proximal ends 111, 131 extending beyond the tunnel 24.

Figure 13:
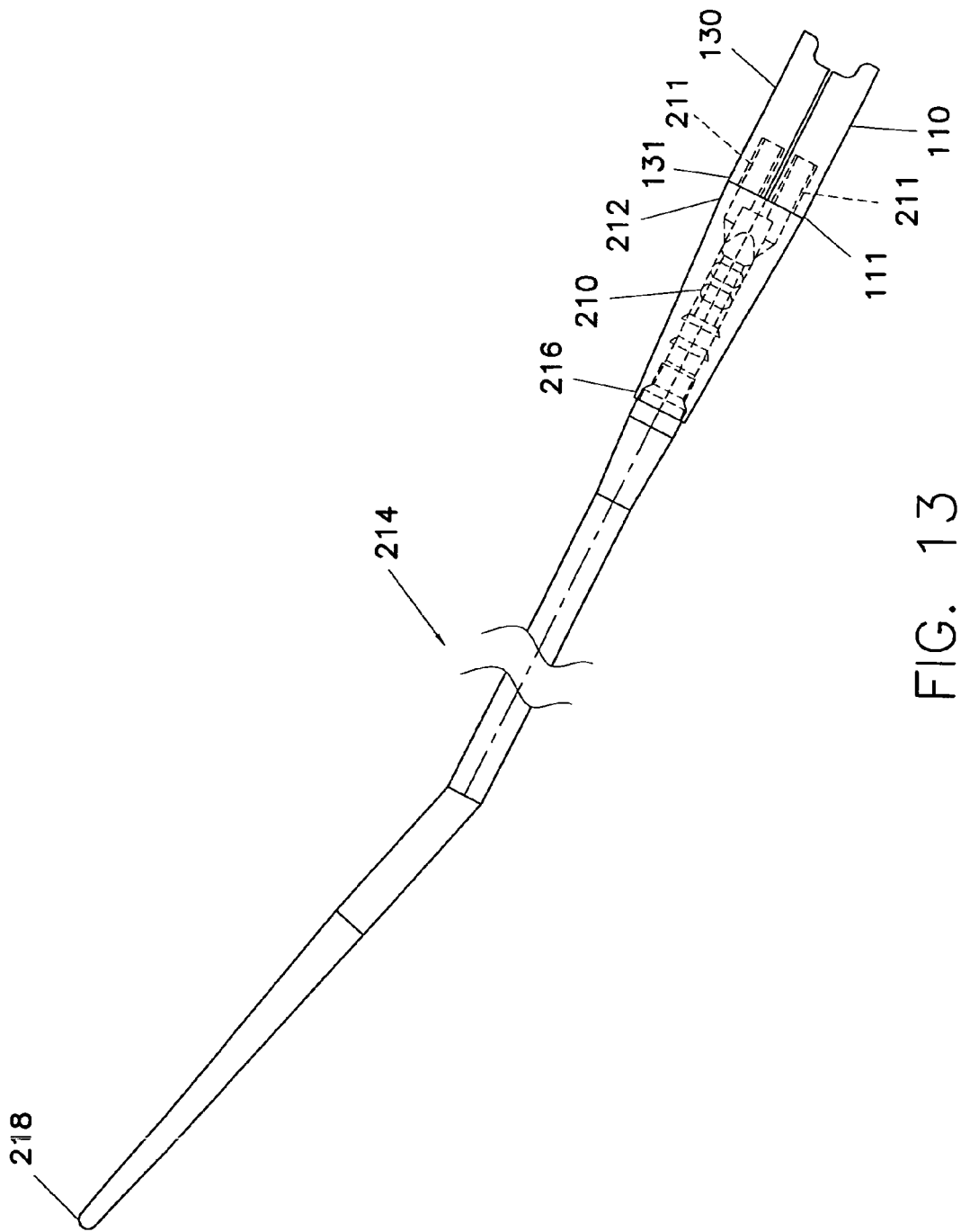
FIG. 13 is a perspective view of a catheter tunneler used to pull the proximate end of the catheters through the subcutaneous tunnel.

A catheter tunneling adapter 210, preferably similar to the catheter tunneling adapter shown in FIG. 13 and disclosed in U.S. Publication No. US 2004/0176739, is releasably connected to the proximal ends 111, 131 of the catheters 110, 130. Alternatively, an adapter such as the adapter disclosed in U.S. Publication No. US 2005/0027282 may be used. Preferably, an extension 211 extending from the first end 212 of the tunneling adapter 210 is inserted into each of the proximal ends 111, 131 of the catheters 110, 130 and a trocar 214 is connected to the second end 216 of the adapter 210. The trocar 214, the adapter 210, and catheters 110, 130 are pulled through the subcutaneous tunnel 24 made by the pointed end 218 of the trocar 214. Once the catheters 110, 130 have been placed in the subcutaneous tunnel 24, and after the adapter 210 and trocar 214 have been removed, the catheters 110, 130 appear as shown in FIG. 11. The ingrowth cuff 125 is disposed within the subcutaneous tunnel 24. Over time, skin tissue forming the wall of the subcutaneous tunnel 24 will grow into the ingrowth cuff 125, securing the catheters 110, 130 in the subcutaneous tunnel 24. It is also seen in FIG. 11, that lengths of the proximal lumen end portions 112, 132 extend proximally from the tunnel 24, and thus provide a range of potential sites for attaching the hub thereto from which the practitioner may choose a desired hub site. It has been previously described that the length of the tunnel may be dependent on the particular patient. Thus, if the proximal lumen ends extend for an unnecessary long distance proximally of the tunnel exit after tunneling, the practitioner may trim them prior to attaching the hub and attaching the extension tube assemblies to the lumen ends.

After the catheter assembly 100 is inserted as shown in FIG. 11, the incision 18 is closed and the cannulating portion 102 of the assembly 100 is substantially below the skin of the patient. Next, the extension tube assemblies 113, 133 are connected to the proximal ends 111, 131 of the first and second catheters 110, 130, respectively.

Figure 9:
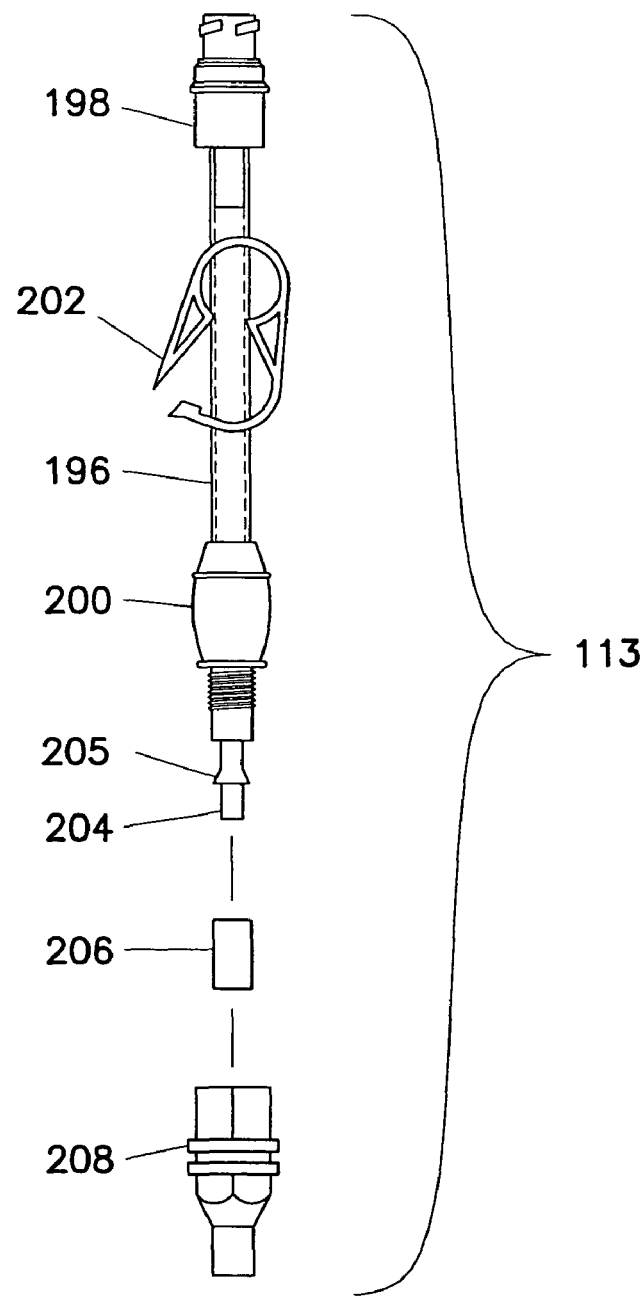
FIG. 9 is an enlarged exploded view of an extension tube assembly according to an embodiment of the present invention.

Regarding the first extension tube assembly 113 and referring to FIGS. 8 and 9, the first female threaded connector portion 208 is first slid over the exterior of the proximal end 111 of the first lumen 110. Next, the first compression fitting 206 is slid over the exterior of the proximal end 111 of the first lumen 110. Then, the first extension tube connector 204 is inserted into the proximal end 111 of the first catheter 110. The first female threaded connector portion 208 is threadingly connected to the first male threaded connector portion 200, such that the compression fitting 206 and the proximal end 111 of the first catheter 110 are securely retained between the first female threaded connector portion 208 and the first extension tube connector 204. The process is repeated for connecting the second extension tube assembly 133 to the second catheter 130.

Now with reference to FIGS. 5 and 6, to further ensure that the proximal catheter end regions 112, 134 remain secured in the subcutaneous area 16 of the body 14, the hub 150 is secured to the assembly 100 by placing the catheters 110, 130 into the bottom hub portion 162 such that the first transition portion 186 is disposed in the first proximal channel 158 and the second transition portion 188 is disposed in the second proximal channel 159, with a portion of the first and second catheters 110, 130 distal of the first and second transition portions 158, 159 being disposed within the distal channel 155. The top hub portion 160 is pivoted about the hinge 151 to the closed position such that the tabs 172 on the top hub 160 portion snap into the recesses 174 in the bottom hub portion 162, securing the hub 150 to the catheters 110, 130. The hub 150 may now be sutured to the patient's skin by suturing the sutures (not shown) over the suture wing assemblies 157. Insertion of the catheter assembly 100 is now complete, as shown in FIG. 12.

Lastly, the open ends of the luer connectors 198, extending caudally from the tunnel 24, are attached in fluid communication with respective fluid inlets and outlets of a hemodialysis unit, or other fluid transfer equipment (not shown), and dialysis can begin.

After the catheter assembly 100 has been inserted into the patient for sufficient time for the ingrowth cuff 125 to become secured within the subcutaneous tunnel 24, the sutures may be cut from the suture wing assemblies 157. The hub 150 may be removed by unsnapping the tabs 172 in the top hub portion 160 from the recesses 174 in the bottom hub portion 162, pivoting the top hub portion 160 about the hinge 151 to open the hub 150, and removing the hub 150 from the rest of the catheter assembly 100.

In an alternative insertion method, the catheters 110, 130 are pulled through the subcutaneous tunnel 24 prior to inserting the distal ends 114, 124 of the catheters 110, 130 into the vessel being catheterized. In this method, the catheter tunneling adapter 210 is connected to the distal ends 114, 134 of the catheters 110, 130 and the pointed end 218 of the trocar 214 is used to form the subcutaneous tunnel 24 and to pull the catheter lumens 110, 130 through the tunnel 24. The pointed end 218 of the trocar 214 exits the skin proximate to the insertion site 20. The trocar 214 and the catheter tunneling adapter 210 are removed and the distal ends 214, 234 of the catheters 210, 230 are inserted into the incision 18 as described above. The extension tube assemblies 113, 133 may be connected to the proximal ends 111, 131 of the catheters 110, 130 prior to or after inserting the catheters 110, 130 into the vessel.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of releasably attaching a hub to a catheter component of a catheter assembly; the method comprising:
   (a) providing a catheter component having a length and at least one lumen;
   (b) providing a releasably attachable hub having two opposing portions each having an inner face, the hub having at least one channel associated with each at least one lumen and disposed on the inner face of at least one of the two opposing portions, and the hub also having a locking section for releasably locking the opposing portions in the closed position;
   (c) then, selecting a hub site from a plurality of potential hub sites along the length of the catheter component;
   (d) then, placing a proximal end region of each at least one lumen of the catheter component at the selected hub site directly into and along a respective at least one channel such that each at least one lumen extends integrally completely along its respective channel and beyond distal and proximal hub portion ends;
   (e) then, placing the other of the two opposing portions over the at least one lumen thereby mating the inner face of one of the two opposing portions with the inner face of the other thereof and fitting the two portions directly around each at least one lumen; and then (f) releasably locking the hub in the closed position with the at least one lumen extending through and beyond the hub to a proximal end of each at least one catheter lumen, whereby a proximal end of each at least one catheter lumen is spaced proximally of the hub and is directly connectable to a medical device at a location spaced proximally of the hub.

2. The method according to claim 1, further comprising longitudinally translating the hub along the proximal end regions of each of the at least one catheter lumen to another selected hub site.

3. The method according to claim 1, further comprising juxtaposing a first lumen against a second lumen in a distal end of the hub and separating the first and second lumens in a proximal end of the hub.

4. The method according to claim 1, further comprising releasably connecting the hub to a patient.

5. The method according to claim 1, further comprising removing the hub from the catheter component by:
(a) unlocking the hub;
(b) uncoupling the two opposing portions; and
(c) moving the hub away from the catheter component.

6. The method according to claim 1, wherein the channels of the hub portions diverge between distal and proximal hub ends, whereby at least one catheter lumen diverges from others thereof between the distal and proximal hub ends.

7. The method according to claim 1, further including the step of connecting an extension tube assembly directly to the proximal end of each at least one catheter lumen at a location spaced proximally of the hub.

8. The method according to claim 1, further including the step, prior to the step of placing the proximal end region of each at least one lumen of a catheter directly into and along a respective at least one channel of the hub, of subcutaneously tunneling the proximal end region of each at least one lumen of the catheter.

9. The method according to claim 8, wherein the catheter includes at least two catheter lumens initially joined together side-by-side, and the method further includes the subsequent step of splitting apart the proximal end regions of the at least two initially joined-together catheter lumens prior to placing the proximal end regions along respective channels of the hub.

10. A method of releasably attaching a hub to a catheter component of a catheter assembly; the method comprising:
(a) providing a catheter component having a length and at least one lumen;
(b) providing a releasably attachable hub having two opposing portions each having an inner face, the hub having at least one channel associated with each at least one lumen and disposed on the inner face of at least one of the two opposing portions, and the hub also having a locking section for releasably locking the opposing portions in the closed position;
(c) then, implanting a distal portion of the catheter component into vasculature of a patient and subcutaneously tunneling the proximal end region of each at least one lumen of the catheter;
(d) then, selecting a hub site from a plurality of potential hub sites along the length of the catheter component proximally of the tunneled catheter portion;
(e) then, placing a proximal end region of each at least one lumen of the catheter component at the selected hub site directly into and along a respective at least one channel such that each at least one lumen extends integrally completely along its respective channel and beyond distal and proximal hub portion ends;
(f) then, placing the other of the two opposing portions over the at least one lumen thereby mating the inner face of one of the two opposing portions with the inner face of the other thereof and fitting the two portions directly around each at least one lumen; and
(f) then, releasably locking the hub in the closed position with the at least one lumen extending through and beyond the hub to a proximal end of each at least one catheter lumen, whereby a proximal end of each at least one catheter lumen is spaced proximally of the hub and is directly connectable to a medical device at a location spaced proximally of the hub.

11. The method according to claim 10, wherein the catheter includes at least two catheter lumens, and the method includes placing the proximal end regions of each thereof along respective channels of the hub.

* * * * *